United States Patent [19]
Yamagishi

[11] Patent Number: 6,043,032
[45] Date of Patent: *Mar. 28, 2000

[54] METHOD OF EXTRACTING NUCLEIC ACIDS AND METHOD OF DETECTING SPECIFIED NUCLEIC ACID SEQUENCES

[75] Inventor: Hiroaki Yamagishi, Kanagawa-ken, Japan

[73] Assignee: Tosoh Corporation, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/745,310

[22] Filed: Nov. 12, 1996

Related U.S. Application Data

[63] Continuation of application No. 08/427,980, Apr. 21, 1995, abandoned, which is a continuation of application No. 08/124,618, Sep. 22, 1993, abandoned.

[51] Int. Cl.$^7$ .............................. C12Q 1/68; C12P 19/34; C07H 21/00
[52] U.S. Cl. ........................... 435/6; 435/91.2; 536/25.4; 536/25.41; 536/25.42
[58] Field of Search ................................. 435/6, 91.2, 4; 935/77, 78; 536/25.4, 25.41, 25.42

[56] References Cited

U.S. PATENT DOCUMENTS 5,422,241  6/1995  Goldrick et al. ............................. 435/6

FOREIGN PATENT DOCUMENTS 0 389 063 A2  9/1990  European Pat. Off. .
0 393 744 A1  10/1990  European Pat. Off. .
0 487 218 A1  5/1992  European Pat. Off. .

OTHER PUBLICATIONS

Analtical Biochemistry vol. 162, 1987 pp. 463–465; Bowtell 'Rapid isolation of eukariotic DNA'.
Higuchi et al., Biotechnology 10:413–417(Apr. 1992).
Goblet et al., Nucleic Acids Research, 17(5):2144 (1989).
Sambrook et al., Molecular Cloning:A Laboratory Manual, 2$^{nd}$ Ed., Cold Spring Harbor Laboratory Press, N.Y. pp E.10–E.11(1989).

*Primary Examiner*—Lisa B. Arthur
*Attorney, Agent, or Firm*—Nixon & Vanderhye

[57] ABSTRACT

An improved method of extracting nucleic acids from a sample comprising mixing the sample with a carrier which is at least one member selected from the group consisting of dextran, acrylamide and carboxymethyl cellulose to form a liquid mixture; mixing said liquid mixture with reagent C to render the nucleic acids and the carrier insoluble, said reagent C containing at least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol, and tert-amyl alcohol; and separating the insolubilized nucleic acids and carrier from the liquid phase. The method is easier to use than the heretofore practiced procedures, involves a smaller number of steps, can reduce the possibility of aerosol generation, can be implemented within a short time, does not use phenol or chloroform, and yet it achieves a consistent efficiency in the extraction of nucleic acids. Also disclosed is a method of detecting a specified nucleic acid sequence.

3 Claims, 8 Drawing Sheets

1 2 3 4 5 6

← a
← b 1 2 3 4 5 6

PCR SOLUTION (AFTER EXTRACTION)

PCR SOLUTION (BEFORE EXTRACTION)

```
                            SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:1:

GGACTTCTCT CAATTTTCTA GGG                                              23

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:2:

CAAATGGCAC TAGTAAACTG AGC                                              23

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:3:

CTCCACCATA GATCACTCCC C                                                21

(2) INFORMATION FOR SEQ ID NO:4:

(i) SEQUENCE CHARACTERISTICS:
         (A) LENGTH: 19 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:4:

GCACTCGCAA GCACCCTAT                                                   19
```

METHOD OF EXTRACTING NUCLEIC ACIDS AND METHOD OF DETECTING SPECIFIED NUCLEIC ACID SEQUENCES

This is a continuation of application Ser. No. 08/427,980, filed Apr. 21, 1995, now abandoned which is a continuation of 08/124,618 filed Sep. 22, 1993 now abandoned.

BACKGROUND OF THE INVENTION

This invention relates to a method of extracting nucleic acids from a sample. More particularly, this invention relates to a method of nucleic acid extraction and a method of specified nucleic acid sequence detection that can be used in biotechnology and clinical diagnosis.

Extracting nucleic acids from a sample is an important operation in biotechnology, clinical diagnosis and other sophisticated fields. For instance, gene recombinant technology requires the isolation of both a vector DNA and the DNA to be cloned and, in order to make a gene assay on genetic diseases and cancer genes, it is necessary to extract nucleic acids from leukocyte cells and the like present in blood.

Nucleic acids generally do not occur as free molecules but rather in bacteria, cells, virus particles, etc. as they are covered with cell membranes and walls which are composed of proteins, lipids and sugars. Nucleic acids themselves form complexes with histone and other proteins. To extract nucleic acids which are present in this manner, the cell membranes and walls covering them must be disrupted and the proteins of the complexes mentioned above denatured or degraded to thereby become soluble, so that the nucleic acids are freed and then extracted.

Nucleic acids are conventionally extracted by one of the following methods:

(i) the so-called proteinase K/phenol method, in which a proteolytic enzyme such as proteinase K or a surfactant is added to disrupt the cell membrane or wall and the protein of a complex of interest is degraded to free nucleic acids; then phenol/chloroform are added and the mixture is centrifuged to have the nucleic acids transferred into the aqueous phase; the aqueous phase is recovered by separation and ethanol, isopropanol or the like is added to the recovered aqueous phase, thereby rendering the nucleic acids insoluble (Molecular Cloning: A Laboratory Manual, Appendices E3–E4, New York, Cold Spring Harbor Laboratory, 1989);

(ii) the so-called AGPC method, in which a liquid mixture of guanidinium isothiocyanate and phenol is added to a sample of interest to disrupt the cell membrane and wall, so that the protein of the complex is denatured to become soluble; nucleic acids are then freed and chloroform is added to transfer the nucleic acids to the aqueous phase; the aqueous phase is recovered by separation and thereafter, ethanol, isopropanol or the like is added to the recovered aqueous phase, thereby rendering the nucleic acids insoluble (Acid Guanidinium-Thiocyanate Phenol-Chloroform Method: Analytical Biochemistry, 162, 156–159, 1987);

(iii) the so-called guanidinium method, in which guanidinium hydrochloride or guanidinium thiocyanate is added to a sample of interest to disrupt the cell membrane and wall, so that the protein of the complex is denatured to become soluble; nucleic acids are then freed and ethanol or the like is added to render the free nucleic acids insoluble (Molecular Cloning: A laboratory Manual, 7.23–7.25, New York, Cold Spring Harbor Laboratory, 1989; and Analytical Biochemistry 162, 463, 1987); and (iv) the so-called sodium iodide method, in which sodium iodide containing glycogen which has affinity for the nucleic acid to be extracted is added to a sample of interest, whereby the cell membrane and wall are disrupted and the protein of the complex is denatured, so that it becomes soluble; nucleic acids are then freed and isopropanol is added to render the free nucleic acids and glycogen insoluble (Nucleic Acid Res., 19 (20), 592, 1991).

The four methods described above have their own disadvantages. The proteinase K/phenol method involves complicated procedures since it takes much time to accomplish degradation with the proteolytic enzyme and because temperature control is necessary to ensure an effective enzyme reaction. Furthermore, phenol and chloroform are toxic chemical reagents (both of them are designated as deleterious substances in the Poisonous and Deleterious Substances Control Law) and to handle them, the use of protective clothes, gloves, gas proof hoods, etc. is necessary. Furthermore, the liquid waste resulting from the extracting procedure must be subjected to a special treatment, requiring extra cost, time and facilities. In addition, great skill is required to recover by separation the aqueous phase into which nucleic acids of interest have been transferred and this makes it difficult to achieve consistent efficiency in the extraction of nucleic acids.

Similar problems occur in the AGPC method in connection with the handling of phenol and chloroform, as well as in the efficiency of extraction that is related to the recovery by separation of the aqueous phase into which nucleic acids of interest have been transferred. In addition, the AGPC method is specifically intended for extracting RNA and unsuitable for extraction of DNA.

In the guanidinium method, ethanol or the like is added to a sample of interest after the addition of guanidinium hydrochloride or the like. In order to prevent a subsequent drop in the concentration of guanidinium in a solution, highly concentrated (ca. 6–8 M) guanidinium must be used but then the chances of a guanidinium salt being deposited will increase (particularly in winter or when room temperature is no more than 20° C.). The deposition of a guanidinium salt may lead to the plugging of pipettes and other equipment used in the addition of guanidinium hydrochloride or the like and this presents a substantial obstacle to any attempt to mechanize the procedure of the guanidinium method. Ethanol or the like is added subsequent to guanidinium hydrochloride, etc. and to render the nucleic acids insoluble, the final concentration of ethanol or the like must be 50–70%. However, the volume of the sample is increased on account of the addition of guanidinium hydrochloride or the like and, hence, even ethanol of high purity (ca. 100%) must be used in an amount at least equal to the liquid mixture of the sample and guanidinium hydrochloride or the like.

The sodium iodide method is subject to a problem in that it requires incubation at 60° C. for solubilizing proteins or the like, which results in a low efficiency of RNA extraction. Another problem is that labile iodide ion ($I^-$) tends to be oxidized by the action of light or the like and to form an iodine molecule ($I_2$). To avoid this, the reagents have to be stored in a cold dark room.

The polymerase chain reaction (PCR) is known as a method of DNA amplification (Molecular Cloning: A Laboratory Manual, Chap. 14, New York, Cold Spring Harbor Laboratory, 1989) that is capable of gene assay (genetic diagnosis) with ultra-high sensitivity. If DNA amplification is successful, PCR has a potential to accomplish amplification by a factor of at least 100 million. However, in view of the possibility for amplification of even one molecule of DNA, the assay result will be adversely affected in the presence of a DNA (exogenous DNA) that should be absent from the PCR nucleic acid sample or the PCR reagent.

One of the causes for the presence of exogenous DNA occurs at the stage where nucleic acids are extracted from the sample of interest to prepare the PCR nucleic acid sample and this also concerns the aerosol that is generated in the procedure of extracting the nucleic acids of interest. The generation of the aerosol is highly likely to occur in the proteinase K/phenol method or the AGPC method since besides the step of adding the reagent to the sample and performing other procedures such as mixing, these methods also require time-consuming procedures such as recovering the aqueous phase by separation. The particles of the aerosol have a diameter of about 20 $\mu$m and their volume is only about $4\times10^{-6}$ $\mu$L. Consider, for example, a patient suffering from hepatitis B; since ca. $10^5$ virus particles can be contained in 1 $\mu$L of blood, one aerosol particle can contain one virus particle. In other words, the aerosol can do serious harm to PCR which is capable of amplifying one molecule of DNA. Therefore, there is a need to reduce the number of treatment steps involved.

In order to minimize the generation of the aerosol in a PCR process, a method has been proposed in European Patent Publication No. 487,218 that a PCR reaction can be carried out in a harmetic state by using an intercalating fluorescent dye (fluorochrome) or the like to quantify a target DNA in a sample. However, the difficulty to minimize the generation of aerosol in an extraction process of nucleic acid from a sample is still remaining.

SUMMARY OF THE INVENTION

The present inventors conducted intensive studies in order to solve the aforementioned problems with the conventional methods of extracting nucleic acids. As a result, they accomplished a novel method of extracting DNA and RNA, which is easy to operate, involves a smaller number of steps, is capable of reducing the possibility of aerosol production, can be implemented within a short time, does not use phenol or chloroform, and which yet achieves a consistent efficiency in the extraction of nucleic acids. Based on this extraction method, the present inventors also accomplished a method by which specified nucleic acid sequences could be detected in a simpler way than the prior art methods and yet avoiding the problem of aerosol contamination.

According to its first aspect, the present invention provides a method of extracting nucleic acids from a sample containing them, which comprises the steps of:

(1) mixing the sample with a carrier which is at least one member selected from the group consisting of dextran, acrylamide and carboxymethyl cellulose to form a liquid mixture;

(2) mixing said liquid mixture with reagent C to render the nucleic acids and the carrier insoluble, said reagent C containing at least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol and tert-amyl alcohol; and (3) separating the insolubilized nucleic acids and carrier from the liquid phase.

According to its second aspect, the present invention provides a method of detecting a specified nucleic acid sequence, which comprises the steps of:

(1) mixing a sample with a carrier which is at least one member selected from the group consisting of dextran, acrylamide and carboxymethyl cellulose to form a liquid mixture;

(2) mixing said liquid mixture with reagent C to render the nucleic acids and the carrier insoluble, said reagent C containing at least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol and tert-amyl alcohol;

(3) separating the insolubilized nucleic acids and carrier from the liquid phase;

(4) converting the separated nucleic acids to DNA by a reverse transcription reaction if they are RNAs;

(5) subjecting the nucleic acids, either separated in step (3) or obtained in step (4), to a PCR reaction in a polymerase chain reaction solution that contains an oligonucleotide probe suitable for amplifying at least a specified sequence, a mononucleotide triphosphate mixture, a polymerase and an intercalating fluorochrome;

(6) measuring the change that occurs in the intensity of fluorescence as a result of the PCR reaction or the change that occurs in the intensity of fluorescence from the reaction solution during the PCR reaction; and (7) determining, on the basis of the change in the intensity of fluorescence, whether a nucleic acid having the specified sequence was present in the sample.

According its third aspect, the present invention provides a reagent set for extracting nucleic acids that contains at least the following carrier and reagent C with one being kept separate from the other:

(1) at least one carrier selected from the group consisting of dextran, acrylamide and carboxymethyl cellulose; and (2) reagent C containing at least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol and tert-amyl alcohol.

DETAILED DESCRIPTION OF THE PREFERRED EMBODIMENTS

Figure 1A:
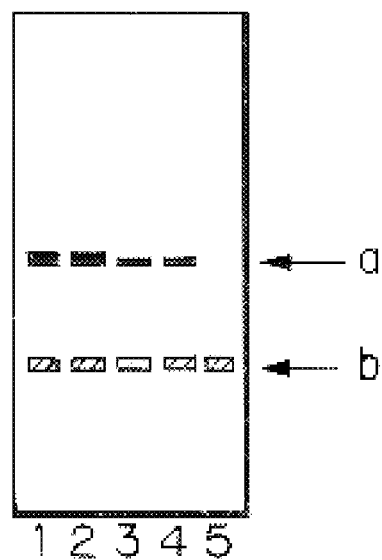
FIG. 1 is a photograph and its diagram showing the results of electrophoresis conducted in the case where the DNA of hepatitis B virus (HBV) extracted by the method of the present invention was amplified by PCR; lanes 1 and 2, HBV rich serum; lanes 3 and 4, HBV lean serum; and lane 5, HBV free serum; band a shows PCR amplification product and band b shows primer oligomer.

The present invention relates to a method of extracting nucleic acids such as single or double-stranded DNA and RNA. Examples of DNA that can be extracted by the method include not only genomic DNA but also the DNA of mitochondrion or chloroplast, and examples of RNA that can be extracted by the method include not only mRNA but also tRNA and rRNA. Samples containing nucleic acids are exemplified by viable samples such as leukocyte cells, the culture of host cells containing vectors or the like that are typically prepared by gene recombinant technology, cells infected with viruses or phages, viruses in blood, and the culture of a sample microorganism. The culture may contain microorganisms but its supernatant alone will do. Not only artificial cultures but also naturally occurring cultures are applicable. In case of samples containing lumps of microorganism, homogenization or sonication may be performed as required to achieve good efficiency of extraction.

According to the first aspect of the present invention, nucleic acids can be extracted from the samples exemplified above; another application of the present invention is for high-yield extraction of amplified nucleic acids from a PCR solution that do not contain enzymes or low-molecular weight deoxynucleotide triphosphate, primers, etc.

The method of the present invention starts with mixing a nucleic acid containing sample with a carrier. Mixing with the carrier helps to form a larger insoluble matter by interwining of nucleic acids and the carrier in the subsequent insolubilizing step of nucleic acids and the carrier by adding reagent C. As a result, the subsequent operation of separating the insoluble matter can be performed in a simplified manner. Thus, the use of the carrier contributes to a higher efficiency of extraction than when no carrier is used.

The carrier has affinity for the nucleic acids to be extracted and is rendered insoluble when it is brought into contact with regent B in reagent C. Since the carrier is extracted along with nucleic acids, it should not interfere with the specific use of the extracted nucleic acids, such as reaction with a restriction enzyme, reverse transcription reaction or PCR. The carrier to be used in the present invention is at least one member selected from the group consisting of dextran, acrylamide and carboxymethyl cellulose. These carriers will prove satisfactorily effective irrespective of whether they are used alone or in admixtures. As a further advantage, they will not interfere with reverse transcription reaction, PCR reaction or any other desired reactions. Glycogen and other conventional carriers will be degraded by amylase or other enzymes contained in the sample if it is serum or blood, with the result that the efficiency of nucleic acid extraction decreases. In contrast, the carrier to be used in the present invention will not be degraded and, hence, there will be no drop in the efficiency of nucleic acid extraction.

The carrier is generally used in an amount of ca. 0.01–1000 μg, preferably ca. 0.1–100 μg, per 10 μl of the sample. The carrier may be placed in a vessel before it is charged with the sample. Alternatively, the sample may be placed into the vessel before charging the carrier. The carrier may be rendered solid by either freeze-drying or air-drying.

In the next step, reagent C is added to the liquid mixture of the sample and the carrier and the ingredients are mixed to render the carrier and nucleic acids insoluble. Reagent C contains at least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol and tert-amyl alcohol.

Reagent C may also contain other reagents such as: a suitable buffer agent for suppressing the degradation of nucleic acids; a chelatant capable of suppressing the activity of nucleases (deoxyribonucleases), as exemplified by sodium citrate and EDTA; a reducing agent for achieving more efficient denaturation and solubilization of proteins, lipids, etc. as exemplified by dithiothreitol and B-mercaptoethanol that reduce disulfide bonds; and a surfactant such as Sarkosyl salt or Triton for achieving more efficient solubilization of proteins, etc. A suitable buffer agent may be added for adjusting the pH of reagent C to the range 4–9, preferably 5–8, so as to prevent the degradation of nucleic acids, thereby achieving a further improvement in the efficiency of their extraction.

In the extraction method of the present invention, at least one compound selected from the group consisting of guanidinium thiocyanate, guanidinium hydrochloride, potassium thiocyanate and sodium thiocyanate is used as reagent A. These compounds disrupt the cell membrane or wall and denature the protein in the complex; they are also capable of solubilizing the denatured protein that forms either as a result of the denaturation of the protein in the complex or on account of concomitant reagent B; at the same time, the compounds are capable of suppressing the activity of nucleases such as deoxyribonuclease and ribonuclease which may be found in the sample. The reagent A to be used in the present invention, either alone or in combination of two or more, has a great ability to solubilize proteins without causing any intefering reactions and, hence, is capable of accomplishing highly efficient extraction of nucleic acids. Commonly known protein denaturing agents such as sodium iodide, potassium iodide, potassium bromide, sodium bromide and urea are not as effective in solubilizing proteins, etc.; on the other hand, guanidinium sulfate, guanidinium carbonate, etc. will cause aggregation of proteins, etc. and, hence, are not capable of highly efficient extraction of nucleic acids.

In the present invention, at least one member selected from the group consisting of n-propanol, isopropyl alcohol, n-butyl alcohol, sec-butyl alcohol, tert-butyl alcohol and tert-amyl alcohol is used as reagent B. When a mixture of two or more alcohols is used, a preferable ratio of the alcohols can be determined by preliminary experiments. The reagent B to be used in the present invention has high solubility in water and will not readily experience phase separation from water; hence, the use of reagent B offers the advantage that the operation of separating the insolubilized nucleic acids and carrier from the aqueous phase can be accomplished in a simple way. This eventually means that the percentage recovery of the insolubilized nucleic acids in the final step of the process can be enhanced.

The concentration of reagents A and B in reagent C may be adjusted in such a way that when reagent C is added to the carrier-containing sample, proteins, lipids, etc. remain solubilized but nucleic acids and the carrier are rendered insoluble. Concentrations that are particularly preferred for the purpose of improving the extraction efficiency are such that the final concentration of reagent as it is added to the sample ranges from 1.5 to 4.5M for reagent A and from about 40 to 80% for reagent B.

For example, in the case where reagent C contains guanidinium thiocyanate as reagent A and isopropyl alcohol as reagent B, the concentration ranges for extracting nucleic acids with a particularly high efficiency are such that the final concentration of reagent A upon mixing with the sample is from 2 to 3M whereas the final concentration of reagent B upon mixing with the sample is from 45 to 55%. If the final concentration of guanidinium thiocyanate is less than 1.5M, proteins, lipids, etc. that are contained in the sample cannot be solubilized fully. In order to increase the final concentration of guanidinium thiocyanate beyond 4.5M, the proportion of reagent A in reagent C must be increased but then reagent A is prone to be solubilized, thereby presenting difficulty in making an appropriate sample preparation. If the final concentration of isopropyl alcohol is less than 40%, the carrier and nucleic acids cannot be rendered completely insoluble. If the final concentration of isopropyl alcohol exceeds 80%, it is difficult to ensure a concentration of guanidinium thiocyanate that is sufficient to achieve complete solubilization of proteins, lipids, etc. and, furthermore, the evaporation of isopropyl alcohol becomes a problem. Hence, it is preferred for the purposes of the present invention to use reagents in the concentration ranges set forth above.

An appropriate amount for the addition of reagent C ranges from 2 to 10 times the volume of the sample if the latter is serum. However, if the sample has high concentrations of proteins, lipids, etc., reagent C is preferably added in an amount more than 10 times the volume of the sample in order to assure complete solubilization of proteins, lipids, etc.

The above-described steps render the nucleic acids and carrier in the sample insoluble; subsequently, the thus insolubilized nucleic acids and carrier are separated from the aqueous phase containing proteins, etc. by performing a conventional separating procedure such as centrifugation or filtration. If centrifugation is performed, nucleic acids can be recovered as pellets on the bottom of the vessel; if filtration is performed, nucleic acids can be recovered on the filtration membrane. The filtration membrane may be of such a type as having pores of about 0.1–10 $\mu$m in size.

The separated nucleic acids can be used as such in various assays and gene recombinant technology but, preferably, they are washed before use. Prewashing is particularly effective when performing an enzyme reaction (e.g. restriction enzyme reaction, reverse transcription reaction or PCR) on the separated nucleic acids and in any other cases where reagent A or the like that is slightly contained in the precipitate may potentially inhibit the enzyme activity which is the prime mover of the reaction. To give a specific example, a solution containing a salt and an alcohol is added to the precipitate obtained by centrifugation or filtration and, after mixing, the preparation is subjected to further centrifugation or filtration. Compared to a case where the precipitate is washed merely with distilled water or the like, washing with a salt/alcohol containing solution has the advantage of contributing to efficient removal of unwanted substances such as reagent A and residual proteins on the surface of pellets. Examples of the salt that can be contained in the washing solution are potassium chloride, sodium chloride and sodium acetate, which may be used in amounts of ca. 0.05–0.5 M; exemplary alcohols include ethanol (which may be contained in an amount of at least 50%, preferably 60–80%), as well as n-propyl alcohol and isopropyl alcohol (which may be contained in an amount of at least 30%, preferably 40–60%).

If there is a particular need to remove any residual proteins from the precipitate, the following procedure may be taken: first, a solution containing reagent A as specified herein is added again to the precipitate so as to solubilize the proteins and, then, a solution containing reagent B as specified herein is added, with the mixture being subjected to further centrifugation or filtration. Needless to say, steps (2) and (3) of the method of the present invention may be simply repeated. When extracting very small amounts of nucleic acids, the present invention is preferably implemented with the sample being maintained at a low temperature by a suitable method such as performing the overall operation in a cold room.

In accordance with the second aspect of the present invention, the thus extracted nucleic acids are checked to see if they contain a specified sequence that is found in nucleic acids such as those of hepatitis B virus or hepatitis C virus and which can be distinguished from other nucleic acids and the invention provides a method of detection that makes use of a technique of DNA amplification which is commonly called the "PCR reaction". Incorporated herein as a reference is the teaching in the specification of European Patent Publication No. 487,218.

In accordance with the method under consideration, if the nucleic acids separated in the manner described hereinabove and preferably washed are RNAs, they are first converted to DNA by reverse transcription reaction. For instance, this is the case of hepatitis C virus, which has RNA as a genome. In the present invention, in order to make use of the PCR reaction for DNA amplification, RNA is converted to the amplifiable DNA prior to the step of amplification to be described below. This step can be accomplished by DNA synthesis in accordance with the ordinary reverse transcription reaction, with the separated RNA being used as a template.

In the next step, the separated nucleic acids or the nucleic acids obtained by reverse transcription reaction in the previous step are subjected to PCR reaction in a polymerase chain reaction solution that contains an oligonucleotide probe, a mononucleotide triphosphate mixture, a polymerase and an intercalating fluorochrome, which probe is at least suitable for amplification of the specified sequence. The oligonucleotide probe in the PCR reaction solution consists of two or more oligonuleotides that have suitable base lengths, that are necessary for producing DNA fragments containing the specified sequence when the PCR reaction progresses, and which are to be located at the 5'-termini of the DNA fragments to be finally produced. A suitable oligonucleotide probe can be selected in accordance with the specified sequence to be detected.

The intercalating fluorochrome that is to be used in the present invention may be exemplified by ethidium bromide, acridine orange, bisbentimide, diaminophenylindole, actinomycin, thiazole, chromomycin and derivatives thereof. The PCR reaction itself has as one cycle the step of operation in which, with the 3'-terminal portions of the specified sequence and a complementary sequence thereto hybridizing with the respective complementary oligonucleotide primers, a reaction for extension from the 5'-terminus to the 3'-terminus is conducted by means of a polymerase, and in which the resulting double strand is dissociated. This cycle may be repeated a suitable number of times.

The change in the intensity of fluorescence is measured for the PCR reaction solution either after or during the PCR reaction. Since the intercalating fluorochrome undergoes a change in its fluorescence characteristics as a result of its incorporation into the double-stranded DNA, the intensity of fluorescence as varying between the start and end of the PCR or during the PCR reaction is an indication as to whether the separated DNA or RNA has the specified sequence.

When implementing the detection method described above, there is no need to supply additional amounts of reagents once the PCR reaction has started. Therefore, in practice, a vessel is first charged with the PCR reaction solution, then charged with the extracted nucleic acids or those which are obtained by subjecting said nucleic acids to reverse transcription reaction; thereafter, the vessel is closed to provide a completely hermetic state, in which the steps of PCR reaction and measurement for the intensity of fluorescence are performed, whereby the probability for the generation of an aerosol can be further reduced.

The present invention also provides a reagent set for implementing the process of nucleic acid extraction which has been described on the foregoing pages. This reagent set contains the carrier and reagent C which have also been described above. The carrier and reagent C are kept separate from each other until use and this may be realized by, for example, placing the carrier and the reagent C in separate containers, the former being in a solid state and the latter in a liquid state.

The reagent set according to the third aspect of the present invention may optionally contain a reaction tube that is made of a suitable plastic material and which is capable of providing a reaction space available for implementing the first aspect of the present invention (method of extracting nucleic acids) or its second aspect (method of detecting a specified nucleic acid sequence). If there is a need not only to extract nucleic acids but also to detect a specified nucleic acid sequence, the reagent set contains preferably a hermetic sealable reaction tube.

The advantage of the reagent set is that if the carrier is preloaded in the tube in a suitable form such as a freeze-dried powder, one only need to add a sample to be assayed and then add reagent C into the tube to initiate the process of extracting nucleic acids and, if necessary, detecting a specified nucleic acid sequence.

The following examples are provided for the purpose of further illustrating the present invention but are in no way to be taken as limiting.

EXAMPLE 1

Extraction from Cultured Cells

Hybridoma cells of mouse myeloma cells and the lymphocyte cells of mice sensitized with CEA (cancer embryonic antigen) were cultivated in a DMEM medium. When the number of fused cells reached $4 \times 10^5$ per ml of the culture solution, a 100-$\mu$l portion of the solution was taken into a sampling tube having a capacity of 0.5 ml. The tube was centrifuged at 7000 rpm for 1 min and the supernatant was removed. The precipitate was resuspended in 20 $\mu$l of a Dulbeco's Modified Eagle Medium. To the suspension, 1 $\mu$l (10 $\mu$g) of dextran (mol. wt., $5 \times 10^5$) was added and mixed; thereafter, 100 $\mu$l of reagent C (2.4 M guanidinium thiocyanate, 15 mM sodium citrate, 0.3% sodium N-lauroyl sarcosine and 60% isopropyl alcohol) was added and the mixture was stirred for ca. 20 sec, followed by 2-min centrifugation at 15000 rpm to have nucleic acids extracted into the precipitate. The supernatant was discarded and 100 $\mu$l of 40% isopropyl alcohol containing 200 mM potassium chloride was added to the precipitate. Following stirring for ca. 20 sec, the mixture was centrifuged at 15000 rpm for 1 min and the supernatant was discarded, whereby more nucleic acids were extracted into the precipitate. The precipitate was assayed by the fluorimetric method of Kissane and Robins (J. Biol. Chem., 233, 184, 1958) to determine the amount of DNA. The precipitate was also subjected to ashing treatment and phosphorus determination was conducted (Anal. Chem., 28, 1756, 1956) to measure the total amount of nucleic acids (DNA+RNA) in the precipitate. The amount of RNA was calculated by subtracting the amount of DNA from the total quantity of nucleic acids (DNA+RNA).

For comparison, nucleic acids were extracted from the same sample by both the proteinase K/phenol method and the AGPC method.

The proteinase K/phenol method was conducted in accordance with the procedure of Keller, G. H. et al. (Anal. Biochem., 170, 441–450, 1988). First, 40 $\mu$l of a reagent (150 mM sodium chloride, 10 mM EDTA, 10 mM Tris with pH of 8, 2% SDS and 250 µg/ml of proteinase K) was added to 20 µl of a cell suspension in a sampling tube having a capacity of 0.5 ml and the mixture was stirred for ca. 20 sec, followed by incubation at 50° C. for 1 h. In the next step, 60 µl of a solution (phenol/chloroform/isoamyl alcohol= 25:24:1) was added and the mixture was stirred for ca. 20 sec, followed by 10-min centrifugation at 15000 rpm. A portion (40 µl) of the supernatant (aqueous phase) was batched off and 8 µl of 4M potassium acetate was added. Further, 10 µg (1 µl) of glycogen and 50 µl of isopropyl alcohol were added and the mixture was stirred, followed by cooling at −20° C. for 30 min. The supernatant was discarded and 100 µl of 75% ethanol was added to the precipitate and the mixture was stirred. Following 20-min centrifugation at 4° C., the supernatant was discarded, whereby nucleic acids were extracted into the precipitate.

The AGPC method was conducted in accordance with the procedure of Chomczymski, P. et al. (Anal. Biochem., 162, 156–159, 1987). First, 40 µl of a reagent (6 M guanidinium thiocyanate, 37.5 mM sodium citrate, 0.75% sodium N-lauroyl sarcosine and 0.15 M 2-mercaptoethanol) was added to 20 µl of a cell suspension in a sampling tube having a capacity of 0.5 ml and the mixture was stirred for ca. 20 sec. Further, 6 µl of 2 M sodium acetate (pH 4) was added and the mixture was stirred for ca. 20 sec. Subsequently, 60 µl of water-saturated phenol was added and the mixture was stirred for ca. 20 sec. In the next step, 12 µl of a solution (chloroform/isoamyl alcohol=49:1) was added and the mixture was stirred for ca. 20 sec. Then, the liquid mixture was cooled in ice water for 15 min and centrifuged at 4° C. for 20 min at 15000 rpm. A portion (60 µl) of the supernatant (aqueous phase) was batched off and 60 µl of isopropyl alcohol was added. The mixture was stirred and cooled at −20° C. for 1 h. Thereafter, the supernatant was discarded and 100 µl of 75% ethanol was added to the precipitate, followed by stirring. In the last step, the mixture was centrifuged at 4° C. for 20 min and the supernatant was discarded, whereby nucleic acids were extracted into the precipitate. The precipitates obtained in the two conventional methods were analyzed by the same procedure as already described above. The results of analysis are shown in Table 1 below. It is clear from Table 1 that the method of the present invention is superior to the two conventional methods in terms of extraction efficiency.

TABLE 1

| Method | DNA (µg) | RNA (µg) | DNA + RNA (µg) |
|---|---|---|---|
| Invention | 2.9 | 1.4 | 4.3 |
| Proteinase K/phenol method | 1.6 | 0.7 | 2.3 |
| AGPC method | 0.2 | 1.0 | 1.2 |

EXAMPLE 2

Extraction from E. coli

E. coli (JM 109) was cultivated in an L-Broth medium. When the number of E. coli cells reached $2 \times 10^8$ per ml of the culture solution, a 1-ml portion of the solution was taken into a 1.5-ml sampling tube and centrifuged at 7000 rpm for 1 min. The supernatant was discarded and the precipitate was suspended in 50 µl of an L-Broth medium. To the suspension, 2 µl (20 µg) of dextran (mol. wt., $5 \times 10^5$) was added and mixed; thereafter, 250 µl of reagent C (2.4M guanidinium thiocyanate, 15 mM sodium citrate, 0.3% sodium N-lauroyl sarcosine and 60% isopropyl alcohol) was added and the mixture was stirred for ca. 20 sec, followed by 2-min centrifugation at 15000 rpm to have nucleic acids extracted into the precipitate. The supernatant was discarded and 250 µl of 40% isopropyl alcohol containing 200 mM potassium chloride was added to the precipitate. Following stirring for ca. 20 sec, the mixture was centrifuged at 15000 rpm for 1 min and the supernatant was discarded, whereby more nucleic acids were extracted into the precipitate. The amount of DNA and the total amount of nucleic acids (DNA+RNA) were measured as in Example 1 and the amount of RNA was calculated. The results are shown in Table 2 below.

TABLE 2

| DNA (µg) | RNA (µg) | DNA + RNA (µg) |
|---|---|---|
| 4.4 | 36.6 | 41.0 |

EXAMPLE 3

Extraction of Hepatitis B Virus DNA

Dextran (1 µl, 10 µg) with mol. wt. of $5 \times 10^5$ was taken into sampling tubes each having a capacity of 0.5 ml and 20 µl of serum from patients with hepatitis B was also taken into the respective tubes. Thereafter, 100 µl of reagent C (2.4 M guanidinium thiocyanate, 15 mM sodium citrate and 60% isopropyl alcohol) was added and the mixture was stirred for ca. 20 sec. By 2-min centrifugation at 15000 rpm, nucleic acids were extracted into the precipitate. The supernatant was discarded and 100 µl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate.

To the precipitate, 25 µl of a PCR reagent (Takara Shuzo Co., Ltd.) was added and PCR was conducted through 40 cycles using a DNA thermal cycler (Perkin-Elmer-Cetus). The conditions of PCR were as follows (the primers identified below were used for specific amplification of nucleic acids in hepatitis B virus, HBV):

| Cycle time | | |
|---|---|---|
| Denaturation | 94° C. | 1 min |
| Annealing | 55° C. | 45 sec |
| Synthesis | 72° C. | 1 min |

Base sequences of primers
5'-GGACTTCTCTCAATTTTCTAGGG-3'(SEQ ID NO: 1)
5'-CAAATGGCACTAGTAAACTGAGC-3'(SEQ ID NO: 2)

Figure 1B:
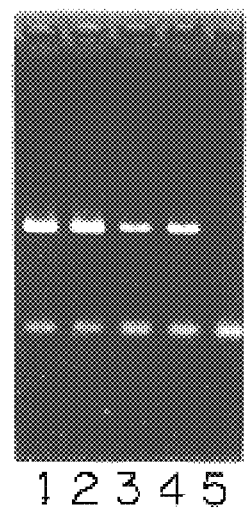

After PCR, the amplified nucleic acids were subjected to electrophoresis and the optical densities of the respective bands were compared by staining with ethidium bromide. The results are shown in FIG. 1.

EXAMPLE 4

Extraction of Hepatitis C Virus RNA

Dextran (1 µl, 10 µg) with mol. wt. of $5 \times 10^5$ was taken into sampling tubes each having a capacity of 0.5 ml and 20 µl of serum from patients with hepatitic C was also taken into the respective tubes. Thereafter, 100 µl of reagent C (2.4 M guanidinium thiocyanate, 15 mM sodium citrate and 60% isopropyl alcohol) was added and the mixture was stirred for ca. 20 sec. By 2-min centrifugation at 15000 rpm, nucleic acids were extracted into the precipitate. The supernatant was discarded and 100 µl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate.

To the precipitate, 10 µl of a reagent for reverse transcription (Takara Shuzo Co., Ltd.) was added and solubilized. Thereafter, a reaction for reverse transcription was conducted with a DNA thermal cycler (Perkin-Elmer-Cetus). The reaction conditions were as follows:

| Annealing | 25° C. | 10 min |
|---|---|---|
| Synthesis | 42° C. | 30 min |
| Inactivation of reverse transcriptase | 99° C. | 5 min |
| Storage | 25° C. | |

Subsequently, 20 µl of a PCR reagent was added to 5 µl of the reverse transcription reaction solution and PCR was conducted through 40 cycles using a DNA thermal cycler (Perkin-Elmer-Cetus). The conditions of PCR were as follows (the primers identified below were used for specific amplification of nucleic acids in hepatitis C virus, HCV):

| Cycle time | | |
|---|---|---|
| Denaturation | 95° C. | 30 sec |
| Annealing | 65° C. | 30 sec |
| Synthesis | 72° C. | 1 min |

Base sequences of primers
5'-CTCCACCATAGATCACTCCCC-3'(SEQ ID NO: 3)
5'-GCACTCGCAAGCACCCTAT-3'(SEQ ID NO: 4)

Figure 2A:
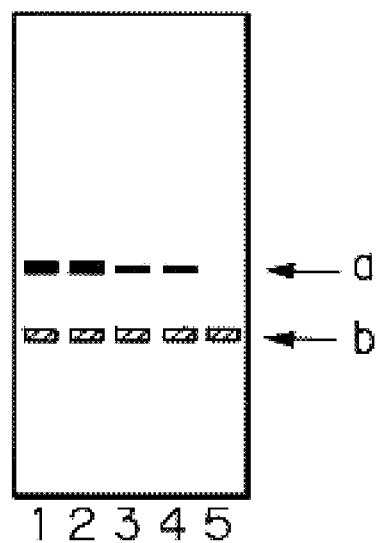
FIG. 2 is a photograph and its diagram showing the results of electrophoresis conducted in the case where the DNA of hepatitis C virus (HCV) extracted by the method of the present invention was amplified by PCR; lanes 1 and 2, HCV rich serum; lanes 3 and 4, HCV lean serum; and lane 5, HCV free serum.
Figure 2B:
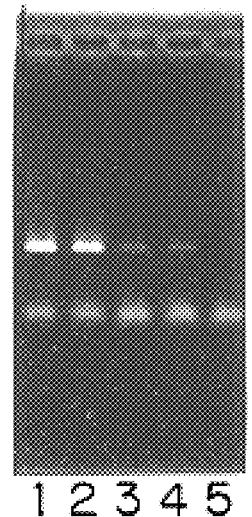

After PCR, the amplified nucleic acids were subjected to electrophoresis and the optical densities of the respective bands were compared by staining with ethidium bromide. The results are shown in FIG. 2.

EXAMPLE 5

Extraction of Hepatitis C Virus RNA

Dextran (2 µl, 20 µg) with mol. wt. of $5 \times 10^5$ was taken into sampling tubes each having a capacity of 1.5 ml and 100 µl of serum from patients with hepatitis C was also taken into the respective tubes. Thereafter, 500 µl of reagent C (2.4 M guanidinium thiocyanate, 15 mM sodium citrate and 60% isopropyl alcohol) was added and the mixture was stirred for ca. 20 sec. By 3-min centrifugation at 15000 rpm, nucleic acids were extracted into the precipitate. The supernatant was discarded and 200 µl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate.

To the precipitate, 20 µl of a reagent for reverse transcription was added and solubilized. Thereafter, a reaction for reverse transcription was conducted under the same conditions as in Example 4. Subsequently, 40 µl of a PCR reagent was added to 10 µl of the reverse transcription reaction solution and PCR was conducted under the same conditions as in Example 4.

For comparison, nucleic acids were extracted by the sodium iodide method (of Ishizawa, M. et al. in Nucleic Acid Res. 19(20): 5792, 1991). First, 100 µl of serum from patients with hepatitis C was taken into sampling tubes each having a capacity of 1.5 ml. Then 300 µl of a reagent (6M NaI, 13 mM EDTA, 0.5% sodium N-lauroyl sarcosine, 10 µg glycogen, and Tris-HCl with pH 8) was added and the mixture was stirred for ca. 20 sec followed by 15-min incubation at 60° C. Thereafter, 400 µl of isopropyl alcohol was added and the mixture was stirred for ca. 20 sec, followed by standing for 15 min. Then, the solution was centrifuged at 15000 rpm for 5 min and the supernatant was discarded. In the next step, 1,000 µl of 40% isopropyl alcohol was added and the mixture was stirred for ca. 20 sec, followed by 5-min centrifugation at 15000 rpm. The supernatant was discarded to have nucleic acids extracted into the precipitate. The precipitate was subjected to reverse transcription reaction and PCR under the same conditions as described in the preceding paragraph. After the end of PCR, 10 µl of the reaction solution was assayed by high-performance liquid chromatography on an apparatus produced by Tosoh Corp. The column was TSK gel, G4000SW for gel permeation chromatography, and UV detection was conducted at 260 nm with UV 8000 (Tosoh Corp.) The eluent was a potassium phosphate buffer (0.1 M, pH 6.8) and its flow rate was 1 ml/min. The results of analysis are shown in Table 3. In accordance with the method of the present invention, the product of amplification by PCR was detected in an average amount of 26 ng per 10 µl of the PCR reaction solution; on the other hand, only 3 ng of the amplification product could be detected by the sodium iodide method.

TABLE 3

| PCR amplification product (ng) | | Average |
|---|---|---|
| Invention | 27 | 26 |
| | 25 | |
| | 26 | |
| Sodium iodide method | 4 | 3 |
| | 3 | |
| | 2 | |

EXAMPLE 6

Extraction of Hepatitis B Virus DNA

Dextran (1 µl, 10 µg) with mol. wt. of $5 \times 10^5$ was taken into a plurality of sampling tubes each having a capacity of 0.5 ml and 20 µl of serum from patients with hepatitis B was also taken into the respective tubes. Various grades of reagent C (see below) were added to the samples and mixed:

(1) 100 µl of reagent C containing 2.4 M guanidinium thiocyanate, 15 mM sodium citrate and 60%, isopropyl alcohol;

(2) 100 µl of reagent C containing 2.4 M potassium thiocyanate, 15 mM sodium citrate and 60%, isopropyl alcohol; and (3) 100 µl of reagent C containing 3.2 M guanidinium hydrochloride, 15 mM sodium citrate and 60%, isopropyl alcohol.

Figure 3A:
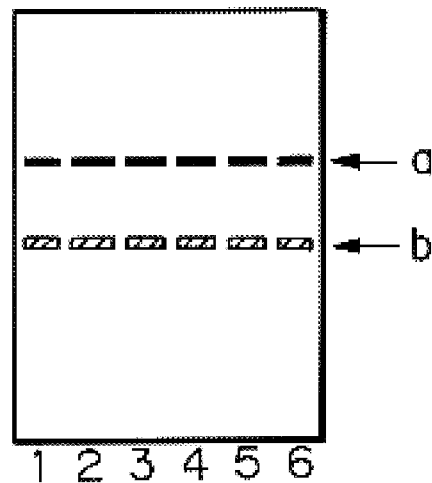
FIG. 3 is a photograph and its diagram showing the results of electrophoresis conducted in the case where the DNA of hepatitis B virus was extracted by the method of the present invention using the various grades of reagent C set forth below; and was amplified by PCR: lanes 1 and 2, (1) reagent C containing 2.4 M guanidinium thiocyanate, 15 mM sodium citrate and 60% isopropyl alcohol; lanes 3 and 4, (2) reagent C containing 2.4 M potassium thiocyanate, 15 mM sodium citrate and 60% isopropyl alcohol; and lanes 5 and 6, (3) reagent C containing 3.2 M guanidinium hydrochloride, 15 mM sodium citrate and 60% isopropyl alcohol.
Figure 3B:
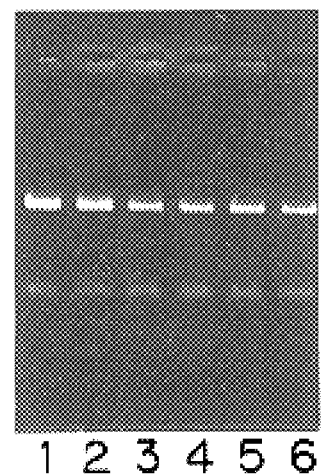

After adding these grades of reagent C and mixing, centrifugation was conducted at 15000 rpm for 2 min so that nucleic acids were extracted into the precipitate. The supernatant was discarded and 100 µl of 40% isopropanol containing 200 mM potassium chloride was added. Following stirring for ca. 20 sec, the mixture was centrifuged at 15000 rpmn for 1 min and the supernatant was discarded to have more nucleic acids extracted into the precipitate. The nucleic acids thus extracted were subjected to PCR under the same conditions as in Example 3. After the end of the reaction, electrophoresis was conducted to compare the optical densities of the respective bands produced. The results are shown in FIG. 3. Obviously, the solutions containing grades (1)–(3) of reagent C produced bands of comparable densities.

EXAMPLE 7

Extraction of Hepatitis B Virus DNA

Dextran (1 μl, 10 μg) with mol. wt. of 5×10$^5$ was taken into a plurality of sampling tubes each having a capacity of 0.5 ml and 20 μl of serum from patients with hepatitis B was also taken into the respective tubes. Various grades of reagent C (see below) were added to the samples and mixed:

(1) 100 μl of reagent C containing 2.4 M guanidinium thiocyanate, 15 mM sodium citrate, 60 mM 2-mercaptoethanol, 0.3% sodium N-lauroyl sarcosine and 60% n-propyl alcohol;

(2) 100 μl of reagent C containing 2.4 M guanidinium thiocyanate, 15 mM sodium citrate, 60 mM 2-mercaptoethanol, 0.3% sodium N-lauroyl sarcosine and 60% isopropyl alcohol;

(3) 80 μl of reagent C containing 3 M guanidinium thiocyanate, 19 mM sodium citrate, 75 mM of 2-mercaptoethanol, 0.38% sodium N-lauroyl sarcosine and 50% n-butyl alcohol;

(4) 100 μl of reagent C containing 2.4 M guanidinium thiocyanate, 15 mM sodium citrate, 60 mM 2-mercaptoethanol, 0.3% sodium N-lauroyl sarcosine and 60% n-butyl alcohol;

(5) 80 μl of reagent C containing 3 M guanidinium thiocyanate, 19 mM sodium citrate, 75 mM 2-mercaptoethanol, 0.38% sodium N-lauroyl sarcosine and 50% sec-butyl alcohol; and (6) 100 μl of reagent C containing 2.4 M guanidinium thiocyanate, 15 mM sodium citrate, 60 mM 2-mercaptoethanol, 0.3% sodium N-lauroyl sarcosine and 60% sec-butyl alcohol.

Figure 4A:
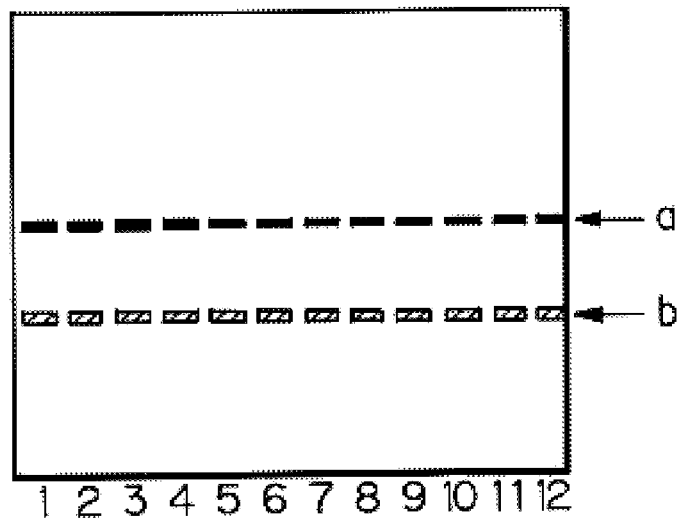
FIG. 4 is a photograph and its diagram showing the results of electrophoresis conducted in the case where the DNA of hepatitis B virus was extracted by the method of the present invention using the reagent C described in Example 7 and was amplified by PCR, with the following types of reagent B being used in the reagent C: lanes 1 and 2, (1) 60% n-propyl alcohol; lanes 3 and 4, (2) 60% isopropyl alcohol; lanes 5 and 6, (3) 50% n-butyl alcohol; lanes 7 and 8, (4) 60% n-butyl alcohol, lanes 9 and 10, (5) 50% sec-butyl alcohol; and lanes 11 and 12, (6) 60% sec-butyl alcohol.
Figure 4B:
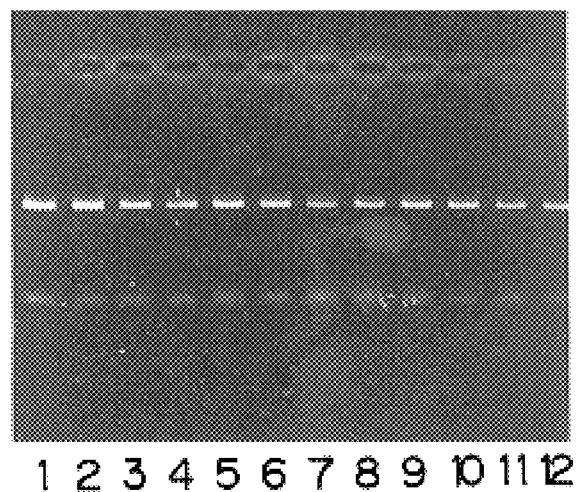

After adding these grades of reagent C and mixing, centrifugation was conducted at 15000 rpm for 2 min so that nucleic acids were extracted into the precipitate. The supernatant was discarded and 100 μl of 40% isopropanol containing 200 mM potassium chloride was added. Following stirring for ca. 20 sec, the mixture was centrifuged at 15000 rpm for 1 min and the supernatant was discarded to have more nucleic acids extracted into the precipitate. The nucleic acids thus extracted were subjected to PCR under the same conditions as in Example 3. After the end of the reaction, electrophoresis was conducted to compare the optical densities of the respective bands. The results are shown in FIG. 4. Obviously, the solutions containing grades (1)–(6) of reagent C produced bands of comparable densities.

EXAMPLE 8

Extraction of Hepatitis B Virus DNA

Dextran (1 μl, 10 μg) with mol. wt. of 5×10$^5$ was taken into a plurality of sampling tubes each having a capacity of 0.5 ml and 20 μl of serum from patients with hepatitis B was also taken into the respective tubes. Various grades of reagent C (see below) were added to the samples and mixed:

(1) 80 μl of reagent C containing 3 M guanidinium thiocyanate, 19 mM sodium citrate, 75 mM 2-mercaptoethanol, 0.38% sodium N-lauroyl sarcosine and 50% tert-amyl alcohol;

(2) 100 μl of reagent C containing 2.4 M guanidinium thiocyanate, 15 mM sodium citrate, 60 mM 2-mercaptoethanol, 0.3% sodium N-lauroyl sarcosine and 60% tert-amyl alcohol;

(3) 100 μl of reagent C containing 2.4 M guanidinium thiocyanate, 15 mM sodium citrate, 60 mM 2-mercaptoethanol, 0.3% sodium N-lauroyl sarcosine and 60% tert-butyl alcohol; and (4) 100 μl of reagent C containing 2.4 M guanidinium thiocyanate, 15 mM sodium citrate, 60 mM 2-mercaptoethanol, 0.3% sodium N-lauroyl sarcosine and 60% isopropyl alcohol.

Figure 5A:
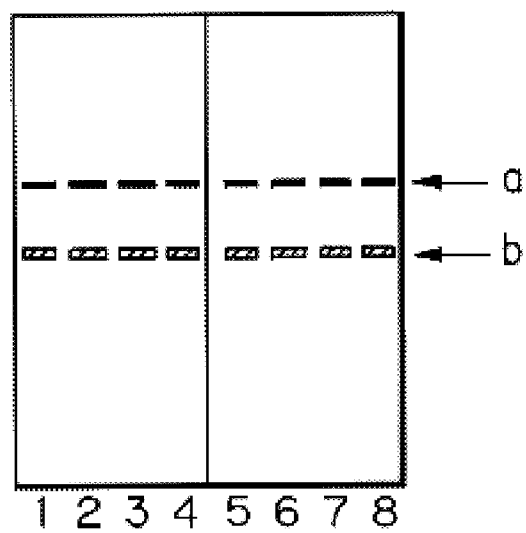
FIG. 5 is a photograph and its diagram showing the results of electrophoresis conducted in the case where the RNA of hepatitis B virus was extracted by the method of the present invention using the reagent C described in Example 8 and was amplified by PCR, with the following types of reagent B being used in the reagent C: lanes 1 and 2, (1) 50% tert-amyl alcohol; lanes 3 and 4, (2) 60% tert-amyl alcohol; lanes 5 and 6, (3) 60% tert-butyl alcohol; and lanes 7 and 8, (4) 60% isopropyl alcohol.
Figure 5B:
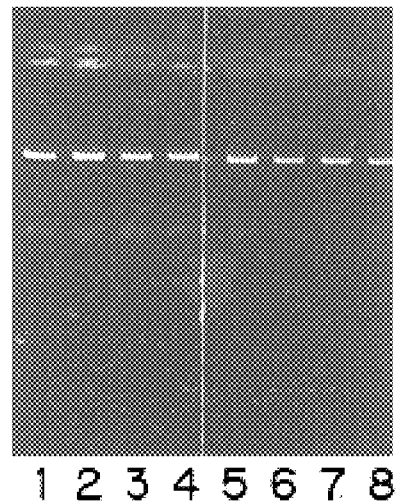

After adding these grades of reagent C and mixing, centrifugation was conducted at 15000 rpm for 2 min so that nucleic acids were extracted into the precipitate. The supernatant was discarded and 100 μl of 40% isopropanol containing 200 mM potassium chloride was added. Following stirring for ca. 20 sec, the mixture was centrifuged at 15000 rpm for 1 min and the supernatant was discarded to have more nucleic acids extracted into the precipitate. The nucleic acids thus extracted were subjected to PCR under the same conditions as in Example 3. After the end of the reaction, electrophoresis was conducted to compare the optical densities of the respective bands. The results are shown in FIG. 5. Obviously, the solutions containing the tested grades of reagent C produced bands of comparable densities.

EXAMPLE 9

Extraction of Hepatitis C Virus RNA

Sampling tubes each having a capacity of 1.5 ml were charged with 0, 0.5, 1, 2 and 5 μl (0, 5, 10, 20 and 50 μg) of a acrylamide solution (mol. wt. ≈7×10$^5$) or 2 μl (20 μg) of dextran with mol. wt. of 5×10$^5$. The tubes were further charged with 100 μl of serum from patients with hepatitis C, and the mixtures were stirred for ca. 5 sec. Then, 500 μl of reagent C (2.4M guanidinium thiocyanate, 15 mM sodium citrate and 60% isopropyl alcohol) was added. Following stirring for ca. 20 sec, 3-min centrifugation was conducted at 15000 rpm so that nucleic acids were extracted into the precipitate. The supernatant was discarded and 200 pl of 40% isopropyl alcohol containing 200 mM potassium chloride was added to the precipitate. Following stirring for ca. 20 sec, 3-min centrifugation was conducted at 15000 rpm and the supernatant was discarded to have more nucleic acids extracted into the precipitate.

To the precipitate, 20 μl of a reagent for reverse transcription was added and solubilized. The solution was subjected to a reaction for reverse transcription under the same conditions as in Example 4. Thereafter, 40 μl of a PCR reagent was added to 10 μl of the reaction solution (for reverse transcription) and PCR was carried out under the same conditions as in Example 4. After the end of PCR, 10 μl of the reaction solution was assayed by high-performance liquid chromatography on an apparatus produced by Tosoh Corp. as in Example 5. The results of analysis are shown in Table 4 below.

TABLE 4

| Amount of acrylamide (μg) | PCR amplification product (ng) |
|---|---|
| 0 | 0 |
| 5 | 26 |
| 10 | 33.5 |
| 20 | 35 |
| 50 | 35 |
| Amount of dextran (μg) | |
| 20 | 44 |

In the absence of acrylamide which is a nucleic acid coprecipitant, the hepatitis C virus RNA was not extracted and, hence, the product of amplification by PCR could not be detected. When acrylamide was added in amounts of 20 μg and more, the product of amplification by PCR was detected in an amount of ca. 35 ng. When 20 μg of dextran was added, the product of amplification by PCR was detected in an amount of ca. 44 ng.

EXAMPLE 10

Extraction of Hepatitis B Virus DNA

Figure 6A:
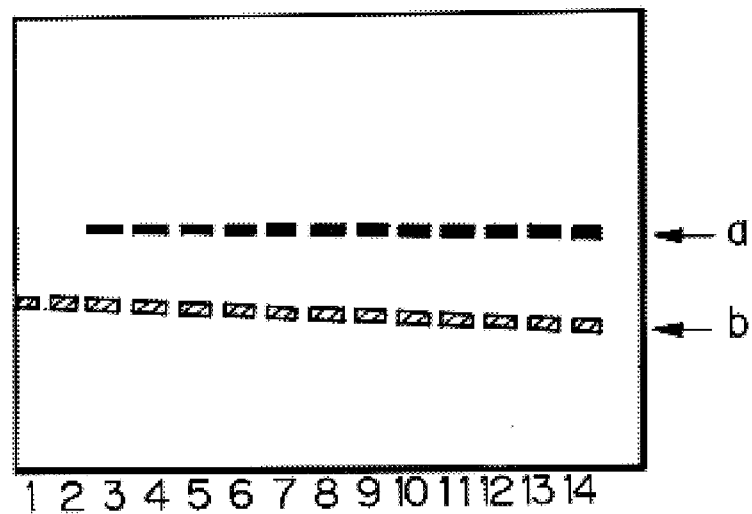
FIG. 6 is a photograph and its diagram showing the results of electrophoresis conducted in the case where the DNA of hepatitis B virus was extracted by the method of the present invention and was amplified by PCR, with dextran being used in the following amounts in the respective tests: lanes 1 and 2, 0 μg; lanes 3 and 4, 2 μg; lanes 5 and 6, 4 μg; lanes 7 and 8, 8 μg; lanes 9 and 10, 16 μg; lanes 11 and 12, 32 μg; and lanes 13 and 14, 64 μg.
Figure 6B:
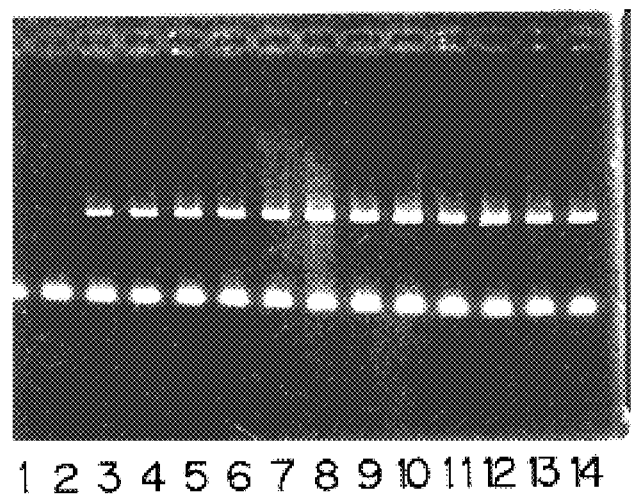

Nucleic acids were extracted and subjected to PCR as in Example 4, except that dextran (mol. wt.=$5\times10^5$) was added in varying amounts of 0, 0.2, 0.4, 0.8, 1.6, 3.2 and 6.4 μl (0, 2, 4, 8, 16, 32 and 64 μg). After the end of PCR, electrophoresis was conducted and the optical densities of bands were compared by staining with ethidium bromide. The results are shown in FIG. 6. Obviously, in the absence of dextran which is a nucleic acid coprecipitant, the hepatitis B virus DNA was not extracted and, hence, no band was detected. When dextran was added in amounts of 16 μg or more, the densities of bands were almost comparable to one another.

EXAMPLE 11

Extraction of Hepatitis B Virus DNA

Figure 7A:
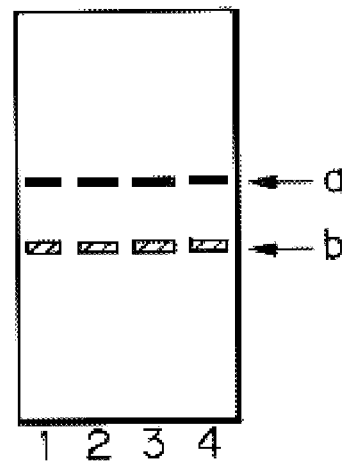
FIG. 7 is a photograph and its diagram showing the results of electrophoresis conducted in the case where the DNA of hepatitis B virus was extracted as in Example 3 using dextran or carboxymethyl cellulose as a carrier and was amplified by PCR; lanes 1 and 2, dextran; and lanes 3 and 4, carboxymethyl cellulose.
Figure 7B:
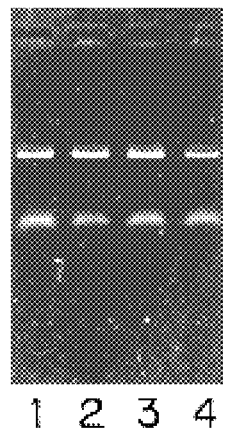

Nucleic acids were extracted and subjected to PCR as in Example 3, except that dextran was replaced by carboxymethyl cellulose (product of SIGMA; Low Viscosity) was used in an amount of 1 μl (10 μg). After the end of PCR, electrophoresis was conducted and the optical densities of bands were compared by staining with ethidium bromide. The result is shown in FIG. 7. Obviously, the band densities were almost comparable when dextran and carboxymethyl cellulose were used as carriers (for reference sake, the result of extraction using dextran is also shown in FIG. 7).

EXAMPLE 12

Application to the Product of PCR Reaction

Sampling tubes each having a capacity of 1.5 ml were charged with 2 μl (20 μg) of a dextran (mol. wt., $5\times10^5$) solution. The tubes were further charged with 20 μl of HBV-PCR reaction solution and 80 μl of water, which were then mixed. Subsequently, 500 μl of reagent C (2.4M guanidinium thiocyanate, 15 mM sodium citrate, 60 mM β-mercaptoethanol and 60% isopropyl alcohol) was added. Following stirring for ca. 20 sec, 3-min centrifugation was conducted at 15000 rpm so that nucleic acids were extracted into the precipitate. The supernatant was discarded and 100 μl of 40% isopropyl alcohol containing 200 mM potassium chloride was added to the precipitate. Following stirring for ca. 20 sec, 3-min centrifugation was conducted at 15000 rpm and the supernatant was discarded to have more nucleic acids extracted into the precipitate. Water (20 μl) was added to the precipitate for its solubilization.

The PCR reaction solution (10 μl), both before and after the extraction of nucleic acids, was analyzed by high-performance liquid chromatography as in Example 5 on an apparatus produced by Tosoh Corp. The column was TSK gel, G3000SW for gel permeation chromatography.

Figure 8B:
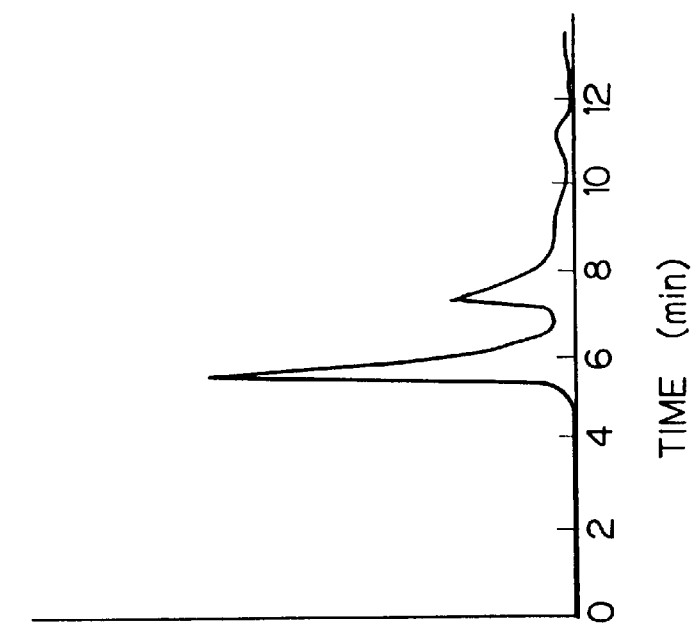
FIG. 8 is a pair of charts showing the results of high-performance liquid chromatography conducted in Example 12 on the PCR reaction solution before nucleic acid extraction (FIG. 8a) and after the extraction (FIG. 8b), with the elution time (in min) being plotted on the horizontal axis and the relative absorbance on the vertical axis.
Figure 8A:
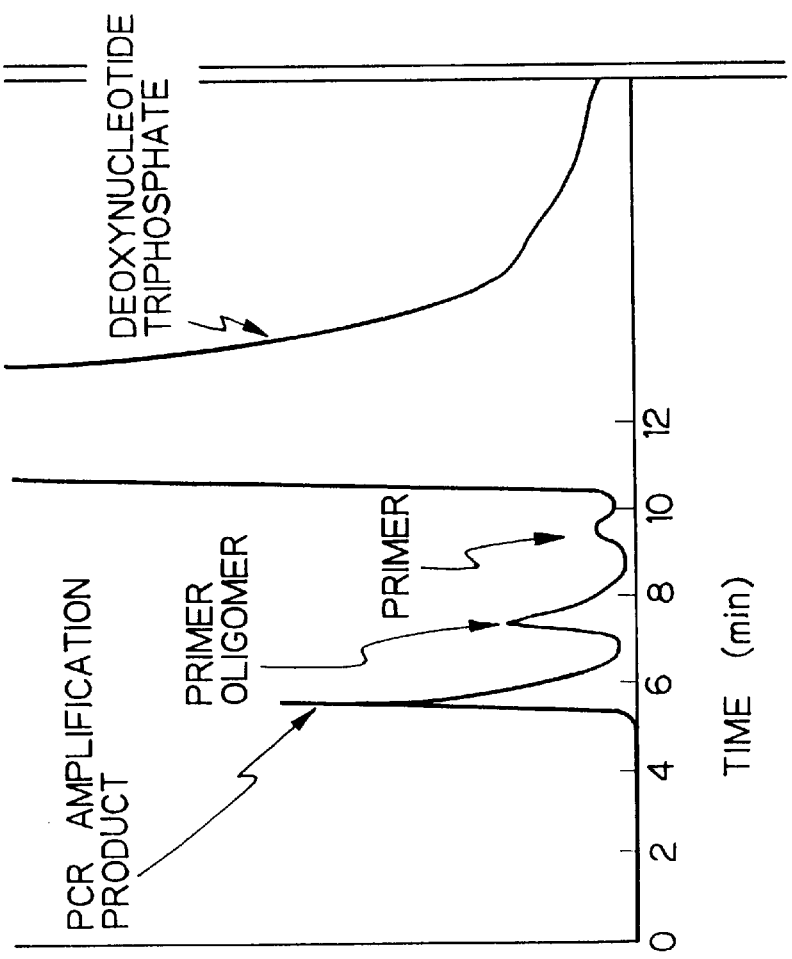

The results are shown in FIG. 8, from which one can see that both the product of amplification by PCR and the primer oligomer were recovered in yields of almost 100%. It is also clear that both the primer and deoxynucleotide triphosphate had been removed.

EXAMPLE 13

PCR Reaction Using Extracted Nucleic Acids

Dextran (2 μl, 20 μg) with mol. wt. of $5\times10^5$ was taken into sampling tubes each having a capacity of 1.5 ml and 100 μl of serum from patients with hepatitis B was also taken into the respective tubes. Then, 500 μl of reagent C (2.4 M guanidinium thiocyanate, 15 mM sodium citrate and 60% isopropyl alcohol) was added and the mixture was stirred for ca. 20 sec. By 3-min centrifugation at 15000 rpm, nucleic acids were extracted into the precipitate. The supernatant was discarded and 200 μl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate. To the precipitate, 50 μl of a PCR reagent was added and PCR reaction was conducted under the same conditions as in Example 3.

For comparison, nucleic acids were extracted by the sodium iodide method (of Ishizawa, M. et al, in Nucleic Acid Res. 19(20): 5792, 1991) as in Example 5 and PCR reaction was conducted in the same manner as just described above. After the end of PCR, 10 μl of the reaction solution was assayed by high-performance liquid chromatography on an apparatus produced by Tosoh Corp. as in Example 5.

The results of analysis are shown in Table 5. In accordance with the method of the present invention, the product of amplification by PCR was detected in an average amount of 7.5 ng per 10 μl of the PCR reaction solution; on the other hand, only 4.3 ng of the amplification product could be detected by the sodium iodide method. The data shown in Table 5 show an average of 4 samples.

TABLE 5

| | PCR amplification product (ng) |
|---|---|
| Invention | 7.5 |
| Sodium iodide method | 4.3 |

EXAMPLE 14

Sampling tubes each having a capacity of 1.5 ml were charged with various carriers:

(1) dextran 2 μl (mol. wt. $5\times10^5$; 20 μg);
(2) dextran 1 μl (mol. wt. $5\times10^5$; 10 μg) and acrylamide 1 μl (mol. wt. $7\times10^5$; 10 μg);
(3) acrylamide 1 μl (mol. wt. $7\times10^5$; 10 μg) and carboxymethyl cellulose 1 μl (10 μg; product of SIGMA; Low Viscosity).

The tubes were further charged with 100 μl of serum from patients with hepatitis B. Then, 500 μl of reagent C (2.4 M guanidinium thocyanate, 15 mM sodium citrate and 60% isopropyl alcohol) was added, and the mixtures were stirred for ca. 20 sec. By 3-min centrifugation at 15000 rpm, nucleic acids were extracted into the precipitate. The supernatant was discarded and 200 μl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate.

To the precipitate, 50 μl of a PCR reagent was added and PCR was carried out under the same conditions as in Example 3. After the completion of PCR, PCR reaction solution was assayed by high-performance liquid chromatography on an apparatus produced by Tosoh Corp. as in Example 5. The results of analysis are shown in Table 6 below. Obviously, a single carrier and a mixture of two carriers produced bands of comparable densities. The data given in Table 6 show an average of 4 samples.

TABLE 6

| Carrier | PCR Amplification product (ng) |
|---|---|
| Dextran | 37 |
| Dextran and acrylamide | 33 |
| Acrylamide and carboxymethyl cellulose | 37 |

EXAMPLE 15

Sampling tubes each having a capacity of 0.5 ml were charged with 2 μl (20 μg) of dextran (mol. wt. 5×10⁵) solution. The tubes were further charged with 100 μl of serum from patients with hepatitis B. Various grades of regent C (see below) were added to the samples and mixed:

(1) 500 μl of reagent C containing 2.4 M guanidinium thiocyanate, 15 mM sodium citrate and 60% isopropyl alcohol;

(2) 500 μl of reagent C containing 2.4 M guanidinium thiocyanate, 15 mM sodium citrate, 30% isopropyl alcohol, and 30% tert-butyl alcohol.

After adding these grades of reagent C and mixing, centrifugation was conducted at 15000 rpm for 3 min so that nucleic acids were extracted into the precipitate. The supernatant was discarded and 200 μl of 40% isopropyl alcohol containing 200 mM potassium chloride was added, followed by stirring for ca. 20 sec and 1-min centrifugation at 15000 rpm. The supernatant was discarded to have more nucleic acids extracted into the precipitate.

To the precipitate, 50 μl of a PCR reagent was added and PCR was carried out under the same conditions as in Example 3. After the completion of PCR, PCR reaction solution was assayed by high-performance liquid chromatography on an apparatus produced by Tosoh Corp. as in Example 5. The results of analysis are shown in Table 7 below. When reagent C contains only isopropyl alcohol, the product of amplification by PCR was detected in an average amount of 42 ng per 10 μl of PCR reaction solution. When reagent C contains isopropyl alcohol and tert-butyl alcohol, the product of amplification by PCR was detected in an average amount of 33 ng per 10 μl of PCR reaction solution. The data given in Table 7 show an average of 2 samples.

TABLE 7

| Alcohol contained in Reagent C | PCR amplification product (ng) |
|---|---|
| Isopropyl alcohol | 42 |
| Isopropyl alcohol and tert-butyl alcohol | 33 |

The present invention offers the following advantages. At least one reagent A selected from the group consisting of guanidinium thiocyanate, guanidinium hydrochloride, potassium thiocyanate and sodium thiocyanate and at least one reagent B selected from the group consisting of n-propyl alcohol, isopropyl alcohol, n-butyl alcohol, sec-butyl alcohol, tert-butyl alcohol and tert-amyl alcohol are preliminarily mixed to prepare reagent C and this helps reduce the amount in which those reagents have to be used. Consider, for example, the case where a 10-μl sample is conditioned in such a way that it will contain a protein denaturing agent and isopropanol in respective final concentrations of 2M and ca. 50%. In the guanidinium method, it is typically required that a 6 M guanidinium solution be added in an amount of 20 μl and then ca. 100% isopropanol be added in an amount of 30 μl. In contrast, the method of the present invention only needs the addition of 20 μl of a nucleic acid extracting reagent that is composed of ca. 75% isopropanol containing 3 M guanidinium thiocyanate. In the guanidinlum method, a 60-μl solution will eventually appear that contains the sample, 2 M guanidinium thiocyanate and ca. 50% isopropanol, whereas only 30 μl of a solution having the same concentration will appear in the present invention. Hence, the amount of the liquid waste that has to be treated after the extraction operation can be reduced accordingly. In addition, the method of the present invention does not have to use poisonous or deleterious substances such as chloroform or phenol and, hence, it can be performed fairly easily compared to the prior art.

In accordance with the first aspect of the present invention, the nucleic acids extracted can be obtained in precipitate and, compared to the prior art which depends upon the difference in the solubility of nucleic acid in two immiscible liquids and in which the liquid phase having the nucleic acid of interest dissolved therein must be separated from the other liquid phase in order to extract the nucleic acid, the present invention can be implemented by extremely simple steps of operation. Therefore, no great skill is needed in the practice of the present invention and yet the desired nucleic acids can be extracted with consistently high efficiency.

As a further advantage, the present invention permits reagent A to be contained at a lower concentration in reagent C that is to be added to the sample and this is effective in preventing the deposition of reagent A. In addition, the concentration of reagent B can also be lowered by a sufficient degree to prevent its evaporation. Hence, the method of the present invention is favorable for the purpose of its mechanized implementation. If reagents A and B are used alone, it is generally difficult to improve the precision of their addition in small portions; however, one may expect that the reagent for extracting nucleic acids according to the present invention can be added with higher precision.

In accordance with the first aspect of the present invention, both the carrier and the reagent C containing reagents A and B are used and, besides the advantages described above, the invention is capable of achieving a higher efficiency of extraction of nucleic acids than the prior art methods.

In accordance with its second aspect, the present invention provides a method of detecting a specified sequence of nucleic acid, which permits a PCR reaction to be carried out and the intensity of fluorescence to be measured within a closed vessel. Therefore, compared to the conventional methods that merely amplify nucleic acids by the PCR procedure and which detect the amplified nucleic acids, the detection method in accordance with the second aspect of the present invention involves a simple procedure of operation and is also capable of reducing the probability of aerosol generation.

What is claimed is:

1. A method of extracting single or double-stranded DNA or RNA from a viable sample or microorganism culture comprising consisting essentially of the steps of:

(a) mixing the sample with a carrier which is at least one member selected from the group consisting of dextran, acrylamide and carboxymethyl cellulose to form a liquid mixture;

(b) mixing said liquid mixture with reagent C to render both the single or double-stranded DNA or RNA and the carrier insoluble and coprecipitate them, said reagent C containing at least one reagent A selected from the group consisting of guanidinium thiocyanate, guanidiniumn hydrochloride, potassium thiocyanate and sodium thiocyanate in a concentration sufficient to disrupt and solubilize cell membranes, wherein the final concentration of reagent A is 1.5 to 3.0M, and at least one reagent B selected from the group consisting of n-propyl alcohol, isopropyl alcohol, n-butyl alcohol, sec-butyl alcohol, term-butyl alcohol and tert-amyl alcohol; and (c) separating the coprecipitated insolubilized DNA or RNA and carrier from the liquid phase.

2. A method of detecting a specified nucleic acid sequence, which consists essentially of the steps of:

(a) mixing a viable sample or microorganism culture with a carrier which is at least one member selected from the group consisting of dextran, acrylamide and carboxymethyl cellulose to form a liquid mixture;

(b) mixing said liquid mixture with reagent C to render both the nucleic acid sequence and the carrier insoluble and coprecipitate them, said reagent C containing at least one reagent A selected from the group consisting of guanidinium thiocyanate, guanidinium hydrochloride, potassium thiocyanate and sodium thiocyanate in a concentration sufficient to disrupt and solubilize cell membranes, wherein the final concentraiton of reagent A is 1.5 to 3.0M and at least one reagent B selected from the group consisting of n-propyl alcohol, isopropyl alcohol, n-butyl alcohol, sec-butyl alcohol, tert-butyl alcohol and tert-amyl alcohol;

(c) separating the coprecipitated insolubilized nucleic acids and carrier from the liquid phase;

(d) converting the separated nucleic acids to DNA by a reverse transcription reaction if they are RNAs;

(e) subjecting the nucleic acids, either separated in step (c) or obtained in step (d), to a PCR reaction in a polymerase chain reaction solution that contains an oligonucleotide probe suitable for amplifying at least a specified sequence, a mononucleotide triphosphate mixture, a polymerase and an intercalating fluorochrome;

(f) measuring the change that occurs in the intensity of fluorescence as a result of the PCR reaction or the change that occurs in the intensity of fluorescence from the reaction solution during the PCR reaction; and (g) determining, on the basis of the change in the intensity of fluorescence, whether a nucleic acid having a specified sequence was present in the sample.

3. A method according to claim 2 wherein the PCR reaction and the measurement of the change in the intensity of fluorescence are performed in a closed vessel which contains the extracted nucleic acids and the PCR reaction solution in a hermetic state.

* * * * *